US007125662B2

(12) United States Patent
Hall et al.

(10) Patent No.: US 7,125,662 B2
(45) Date of Patent: Oct. 24, 2006

(54) METHOD OF IDENTIFYING PUTATIVE ANTIBIOTIC RESISTANCE GENES

(75) Inventors: Barry G. Hall, Rochester, NY (US); Miriam Barlow, Rochester, NY (US)

(73) Assignee: University of Rochester, Rochester, NY (US)

( * ) Notice: Subject to any disclaimer, the term of this patent is extended or adjusted under 35 U.S.C. 154(b) by 716 days.

(21) Appl. No.: 09/950,492

(22) Filed: Sep. 11, 2001

(65) Prior Publication Data
US 2004/0197776 A1 Oct. 7, 2004

Related U.S. Application Data

(60) Provisional application No. 60/231,904, filed on Sep. 11, 2000.

(51) Int. Cl.
*C12Q 1/68* (2006.01)
(52) U.S. Cl. .................. 435/6; 435/69.1; 435/473; 435/476
(58) Field of Classification Search ............. 435/69.1, 435/473, 476, 6, 252.3, 173.6, 252.33; 436/320.1
See application file for complete search history.

(56) References Cited

U.S. PATENT DOCUMENTS

| | | | |
|---|---|---|---|
| 5,605,793 | A | 2/1997 | Stemmer |
| 5,663,317 | A | 9/1997 | Falkow et al. |
| 5,766,842 | A | 6/1998 | Melnick et al. |
| 6,063,562 | A | 5/2000 | Melnick et al. |
| 6,130,036 | A | 10/2000 | Loeb et al. |
| 2001/0014444 | A1 | 8/2001 | Melnick et al. |
| 2001/0044101 | A1 | 11/2001 | Melnick et al. |

FOREIGN PATENT DOCUMENTS

| | | |
|---|---|---|
| WO | WO 96/08580 | 3/1996 |
| WO | WO 00/10582 | 3/2000 |

OTHER PUBLICATIONS

Kleckner et al Uses of Transposons with Emphasis on Tn10. Methods in Enzymology, vol. 204, pp. 139-180, 1991.*
Goyshin et al Insertional transposon mutagenesis by electroporation of released Tn5 transposition complexes. Nature Biotechnology, vol. 18, pp. 97-100, Jan. 2000.*
Miller et al. Genetic Rleationship between soxRS and mar Loci in promoting multiple antibiotic resistance in *E. coli*. Antimicrobial agents and chemotherapy. vol. 38, No. 8, pp. 1773-1779, Aug. 1994.*
Gonzalez Leiza et al. Gene sequence and biochemical characterization of FOX-1 from *Klebsiella pneumoniae* . . . Antimicrobial agents and chemotherapy, vol. 38, No. 9, pp. 2150-2157, Sep. 1994.*
Varela et al. Nucleotide and deduced protein sequences of the class D tetracycline Resistance Determininats.. Antimicrobial agents and chemotherapy, Jun. 1993, vol. 37, No. 6, pp. 1253-1258.*
Wang et al. Characterixation of a Bacteroides mobilizable transposon, NBU2, which carries a functional lincomycin resistance gene. Journal of Bacteriology, vol. 182, No. 12, pp. 3559-3571, Jun. 2000.*
Clermont et al., Identification of Chromosomal Antibiotic Resistance Genes in *Streptococcus anginosus* ("S. milleri"), Antimicrobial Agents and Chemotherapy, 34(9): 1685-1690, (Sep. 1990).
Hall, "Experimental Evolution of Ebg Enzyme Provides Clues About the Evolution of Catalysis and to Evolutionary Potential," *FEMS Microbiology Letters* 174:1-8 (1999).
Hall, "Toward an Understanding of Evolutionary Potential," *FEMS Microbiology Letters* 178:1-6 (1999).
Zhao et al., "Optimization of DNA Shuffling for High Fidelity Recombination," *Nucleic Acids Research* 25(6):1307-1308 (1997).
Zhao et al., "Functional and Nonfunctional Mutations Distinguished by Random Recombination of Homologous Genes," *Proc. Natl. Acad. Sci. USA* 94:7997-8000 (1997).
Zhang et al., "Directed Evolution of a Fucosidase from a Galactosidase by DNA Shuffling and Screening," *Proc. Natl. Acad. Sci. USA* 94:4504-4509 (1997).
Yano et al., "Directed Evolution of an Aspartate Aminotransferase with New Substrate Specificities," *Proc. Natl. Acad. Sci. USA* 95:5511-5515 (1998).
Harayama, "Artificial Evolution by DNA Shuffling," *Tibtech* 16:76-82 (1998).
Stemmer, "Rapid Evolution of a Protein *In Vitro* by DNA Shuffling," *Nature* 370(4):389-391 (1994).
Christians et al., "Directed Evolution of Thymidine Kinase for AZT Phosphorylation Using DNA Family Shuffling," *Nature Biotechnology* 17:259-264 (1999).
Sirawaraporn et al., "Antifolate-Resistant Mutants of *Plasmodium falciparum* Dihydrofolate Reductase," *Proc. Natl. Acad. Sci. USA* 94:1124-1129 (1997).
Crameri et al., "Molecular Evolution of an Arsenate Detoxification Pathway by DNA Shuffling," *Nature Biotechnology* 15:436-438 (1997).
Stanssens et al. "Efficient Oligonucleotide-Directed Construction of Mutations in Expression Vectors by the Grapped Duplex DNA Method Using Alternating Selectable Markers," *Nucleic Acids Research* 17(12):4441-4454 (1989).

(Continued)

*Primary Examiner*—Kenneth R. Horlick
(74) *Attorney, Agent, or Firm*—Nixon Peabody LLP

(57) ABSTRACT

The present invention relates to methods of identifying putative antibiotic resistance genes. According to one embodiment, this is carried out by first isolating a microbial DNA molecule or cDNA which encodes a putative antibiotic resistance protein or polypeptide and then determining whether the microbial DNA molecule or cDNA confers resistance against an antibiotic agent. According to another embodiment, this is carried out by first determining whether a microbial DNA molecule or cDNA confers resistance against an antibiotic agent when the microbial DNA molecule is expressed in its native cell following transformation of the cell and then isolating the microbial DNA molecule or cDNA which confers resistance against the antibiotic agent.

28 Claims, 5 Drawing Sheets

OTHER PUBLICATIONS

Vakulenko et al., "Selection and Characterization of β-Lactam-β-Lactamase Inactivator Resistant Mutants Following PCR Mutagenesis of the TEM-1 β-Lactamase Gene," *Antimicrobial Agents and Chemotherapy* 42(7):1542-1548 (1998).

Vaillancourt et al., "The HIV Type 1 Protease Inhibitor Saquinavir Can Select for Multiple Mutations that Confer Increasing Resistance," *AIDS Research and Human Retroviruses* 15(4):355-363 (1999).

Crameri et al., "DNA Shuffling of a Family of Genes from Diverse Species Accelerates Directed Evolution," *Nature* 391:288-291 (1998).

Canica et al., "Phenotypic Study of Resistance of β-Lactamase-Inhibitor-Resistant TEM Enzymes Which Differ by Naturally Occurring Variations and by Site-Directed Substitution at $Asp_{276}$," *Antimicrobial Agents and Chemotherapy* 42(6):1323-1328 (1998).

Reetz et al., "Superior Biocatalysts by Directed Evolution," *Topics in Current Chemistry* 200:31-57 (1999).

Goryshin et al., "Tn5 *in Vitro* Transposition," *J. Biol. Chem.* 273:7367-7374 (1998).

Davies et al., "Three-Dimensional Structure of the Tn5 Synaptic Complex Transposition Intermediate," *Science* 289:77-85 (2000).

Goryshin et al., "Insertional Transposon Mutagenesis by Electroporation of Released Tn5 Transposition Complexes," *Nat. Biotechnol.* 18:97-100 (2000).

York et al., "Simple and Efficient Generation *in vitro* of Nested Deletions and Inversions: Tn5 Intramolecular Transposition," *Nucl. Acids Res*, 26:1927-1933 (1988).

Metcalf et al., "Use of the *Rep* Technique for Allele Replacement to Construct New *Escherichia coli* Hosts for Maintenance of R6Kγ Origin Plasmids at Different Copy Numbers," *Gene* 138:1-7 (1994).

Reznikoff et al., "Tn5 *lacZ* Translation Fusion Element: Isolation and Analysis of Transposition Mutants," *Methods In Enzymology* 217:312-22 (1993).

Chow et al., "Tn5tac1, a Derivative of Transposon Tn5 that Generates Conditional Mutations," *Proc. Natl. Acad. Sci. USA* 85:6468-6472 (1988).

\* cited by examiner

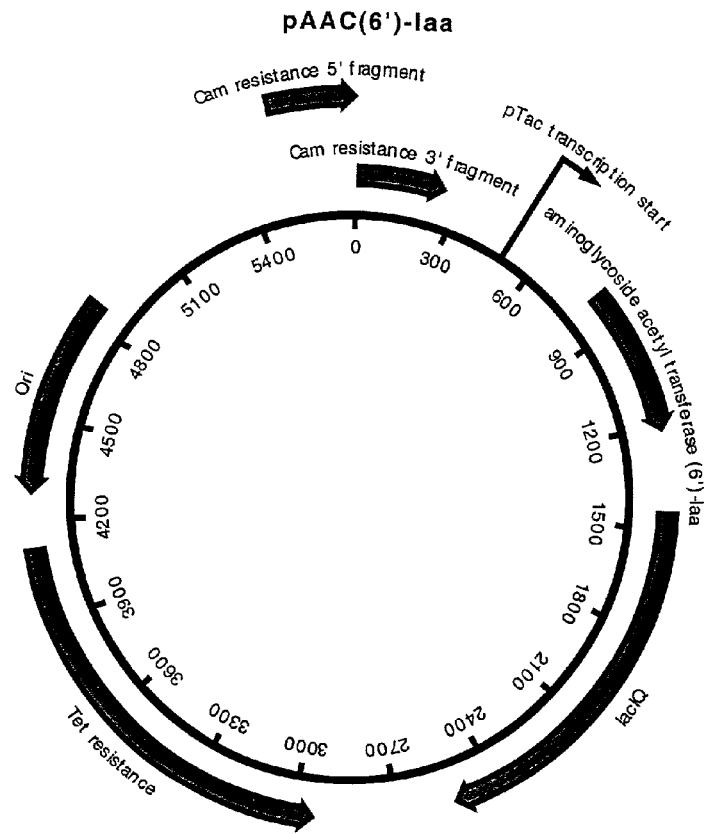

Figure 2A

```
ATGGACATCA GGCAAATGAA CAGAACCCAT CTGGATCACT GGCGCGGATT
GCGAAAACAG CTCTGGCCTG GTCACCCGGA TGACGCCCAT CTGGCGGACG
GCGAAGAAAT TCTGCAAGCC GATCATCTGG CATCATTTAT TGCGATGGCA
GACGGGGTGG CGATTGGCTT TGCGGATGCC TCAATCCGCC ACGATTATGT
CAATGGCTGT GACAGTTCGC CCGTGGTTTT CCTTGAAGGT ATTTTTGTTC
TCCCCTCATT CCGTCAACGC GGCGTAGCGA ACAATTGAT TGCAGCGGTG
CAACGATGGG GAACGAATAA AGGGTGTCGG GAAATGGCCT CCGATACCTC
GCCGGAAAAT ACAATTTCCC AGAAAGTTCA TCAGGCGTTA GGATTTGAGG
AAACAGAGCG CGTCATTTTC TACCGAAAGC GTTGTTGA
```

Figure 2B

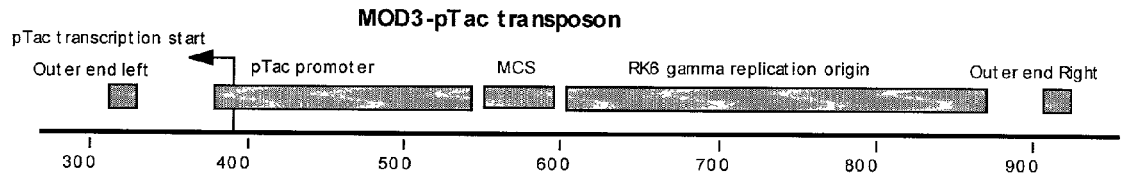

Figure 3A

```
ATTCAGGCTG CGCAACTGTT GGGAAGGGCG ATCGGTGCGG GCCTCTTCGC
TATTACGACA GCTGTCTCTT ATACACATCT CAACCATCAT CGATGAATTT
TCTCGGGTGT TCTCGCATAT TGGCTCGAAT TCATCCGCTC ACAATTCCAC
ACATTATACG AGCCGGATGA TTAATTGTCA ACAGCTCATT TCAGAATATT
TGCCAGAACC GTTATGATGT CGGCGCAAAA AACATTATCC AGAACGGGAG
TGCGCCTTGA GCGACACGAA TTATGCAGTG ATTTACGACC TGCACAGCCA
TACCACAGCT TCCGATGGCT CCCGGGGATC CTCTAGAGTC GACCTGCAGG
CATGCAAGCT TTAAAAGCCT TATATATTCT TTTTTTTCTT ATAAAACTTA
AAACCTTAGA GGCTATTTAA GTTGCTGATT TATATTAATT TTATTGTTCA
AACATGAGAG CTTAGTACGT GAAACATGAG AGCTTAGTAC GTTAGCCATG
AGAGCTTAGT ACGTTAGCCA TGAGGGTTTA GTTCGTTAAA CATGAGAGCT
TAGTACGTTA AACATGAGAG CTTAGTACGT GAAACATGAG AGCTTAGTAC
GTACTATCAA CAGGTTGAAC TGCCAACGAC TACGCACTAG CCAACAAGAG
CTTCAGGGTT GAGATGTGTA TAAGAGACAG CTGTCTTAAT GAATCGGCCA
ACGCGCGGGG AGAGGCGGTT TGCGTATTGG GCGCTCTTCC GCTTCCTCGC
TCACTGAC
```

Figure 3B

```
ATTCAGGCTG CGCAACTGTT GGGAAGGGCG ATCGGTGCGG GCCTCTTCGC
TATTACGACA GCTGTCTCTT ATACACATCT CAACCATCAT CGATGAATTT
TCTCGGGTGT TCTCGCATAT TGGCTCGAAT TCATCCGCTC ACAATTCCAC
ACATTATACG AGCCGGATGA TTAATTGTCA ACAGCTCATT TCAGAATATT
TGCCAGAACC GTTATGATGT CGGCGCAAAA AACATTATCC AGAACGGGAG
TGCGCCTTGA GCGACACGAA TTATGCAGTG ATTTACGACC TGCACAGCCA
TACCACAGCT TCCGATGGCT CCCGGGGATC CTCTAGAGTC GACCGTAAGT
TGGCAGCATC ACCCGACGCA CTTTGCGCCG AATAAATACC TGTGACGGAA
GATCACTTCG CAGAATAAAT AAATCCTGGT GTCCCTGTTG ATACCGGGAA
GCCCTGGGCC AACTTTTGGC GAAAATGAGA CGTTGATCGG CACGTAAGAG
GTTCCAACTT TCACCATAAT GAAATAAGAT CACTACCGGG CGTATTTTTT
GAGTTATCGA GATTTTCAGG AGCTAAGGAA GCTAAATGG AGAAAAAAT
CACTGGATAT ACCACCGTTG ATATATCCCA ATGGCATCGT AAAGAACATT
TTGAGGCATT TCAGTCAGTT GCTCAATGTA CCTATAACCA GACCGTTCAG
CTGGATATTA CGGCCTTTTT AAAGACCGTA AGAAAAATA AGCACAAGTT
TTATCCGGCC TTTATTCACA TTCTTGCCCG CCTGATGAAT GCTCATCCGG
AATTCCGTAT GGCAATGAAA GACGGTGAGC TGGTGATATG GGATAGTGTT
CACCCTTGTT ACACCGTTTT CCATGAGCAA ACTGAACGT TTTCATCGCT
CTGGAGTGAA TACCACGACG ATTTCCGGCA GTTTCTACAC ATATATTCGC
AAGATGTGGC GTGTTACGGT GAAAACCTGG CCTATTTCCC TAAAGGGTTT
ATTGAGAATA TGTTTTTCGT CTCAGCCAAT CCCTGGGTGA GTTTCACCAG
TTTTGATTTA AACGTGGCCA ATATGGACAA CTTCTTCGCC CCCGTTTTCA
CCATGGGCAA ATATTATACG CAAGGCGACA AGGTGCTGAT GCCGCTGGCG
ATTCAGGTTC ATCATGCCGT CTGTGATGGC TTCCATGTCG GCAGAATGCT
TAATGAATTA CAACAGTACT GCGATGAGTG GCAGGGCGGG GCGTAATTTT
TTTAAGGCAG TTATTGGTGC CCTTAAACGC CTGGTGCTAC GCCTGAATAA
GTGATAATAA GCGGATGAAT GGCAGAAATT CGAAAGCAAA TTCGACCCGG
TCGTCGGTTC AGGGCAGGGT CGTTAAATAG CCGCTTATGT CTATTGCTGG
TTTACCGGTT TATTGACTAC CGGAAGCAGT GTGACCGTGT GCTTCTCAAA
TGCCTGAGGC CAAGCTTTAA AAGCCTTATA TATTCTTTTT TTTCTTATAA
AACTTAAAAC CTTAGAGGCT ATTTAAGTTG CTGATTTATA TTAATTTTAT
TGTTCAAACA TGAGAGCTTA GTACGTGAAA CATGAGAGCT TAGTACGTTA
GCCATGAGAG CTTAGTACGT TAGCCATGAG GGTTTAGTTC GTTAAACATG
AGAGCTTAGT ACGTTAAACA TGAGAGCTTA GTACGTGAAA CATGAGAGCT
TAGTACGTAC TATCAACAGG TTGAACTGCC AACGACTACG CACTAGCCAA
CAAGAGCTTC AGGGTTGAGA TGTGTATAAG AGACAGCTGT CTTAATGAAT
CGGCCAACGC GCGGGGAGAG GCGGTTTGCG TATTGGGCGC TCTTCCGCTT
CCTCGCTCAC TGAC
```

Figure 4B

METHOD OF IDENTIFYING PUTATIVE ANTIBIOTIC RESISTANCE GENES

This application claims the benefit of U.S. Provisional Patent Application Ser. No. 60/231,904, filed Sep. 11, 2000, which is hereby incorporated by reference in its entirety.

This invention was made, at least in part, utilizing funding received from the National Institutes of Health grant number GM60761. The U.S. government may have certain rights in this invention.

FIELD OF THE INVENTION

The present invention relates to approaches for identifying previously unidentified or putative antibiotic resistance genes in bacteria.

BACKGROUND OF THE INVENTION

Antibiotics have proven to be one of medicine's most effective tools in combating disease, but their utility is constantly being challenged by the emergence of antibiotic-resistant target organisms and their future effectiveness is now in doubt. The pharmaceutical industry responds to a newly-emerged resistant strain by developing a modified version of the drug that was effective against a predecessor of the newly-emerged resistant strain, and in turn pathogens evolve resistance to the new drug. Some of the best evidence that drug resistance genes can evolve by mutation to confer resistance to newer drugs comes from the TEM/SHV β-lactamases in which genes that originally did not confer resistance to $2^{nd}$ and $3^{rd}$ generation cephalosporins evolved the ability to do so as the result of base substitution mutations. The products of those evolved genes are called extended-spectrum β-lactamases (ESBL's). The example of ESBL's has led to a paradigm according to which the acquisition of resistance to new drugs will almost always involve evolution of known drug resistance genes as the result of selectively advantageous mutations.

This paradigm ignores the issue of the ultimate source of antibiotic resistance genes. Understanding the origins of antibiotic resistance genes may be an essential key to predicting how resistance to new drugs will arise.

In most cases, the source of resistance genes is unknown. Most resistance genes were originally detected on plasmids and, although they spread from plasmid-to-plasmid and via plasmids from one bacterium to another, their original source cannot readily be determined. The ampC β-lactamase genes, whose products are the Class C β-lactamases, provide a rare exception to the ignorance of resistance gene origins.

Class C β-lactamases are generally quite active toward cephalosporins, including the third generation derivatives, but have not been taken as a serious threat until recently, because the genes for Class C β-lactamases are typically located on chromosomes rather than on plasmids. The chromosomal ampC genes are found in a variety of Gram negative bacteria, including both the Enterobacteriaceae and *Pseudomonas* species. ampC genes are typically expressed at a low level, as in *E. coli*, or are inducible by penicillins and early generation cephalosporins but not inducible by third and fourth generation cephalosporins. Over the last decade, however, it has been found that Gram negative pathogens that are hyper-producers of ampC β-lactamases are resistant to all but a few of the most recently introduced β-lactam antibiotics (Livermore, "Are all Beta-lactams Created Equal?" *Scand. J. Infect. Dis. Suppl.* 101:33–43 (1996)). By now 25–50% of *Enterobacter* isolates from intensive care unit patients in many major Western and Far Eastern hospitals are AmpC hyper-producers and are resistant to all penicillins and cephalosporins except imipenem, meropenem and temocillin (Livermore, "Are all Beta-lactams Created Equal?" *Scand. J. Infect. Dis. Suppl.* 101: 33–43 (1996)). Even more worrying are several recent reports of de-repressed ampC genes located on plasmids found in pathogenic Gram negative bacteria (Bauernfeind et al., "Characterization of the Plasmidic Beta-lactamase CMY-2, which is Responsible for Cephamycin Resistance," *Antimicrob. Agents Chemother.* 40:221–224 (1996); Horii et al., "Characterization of a Plasmid-borne and Constitutively Expressed blaMOX-1 Gene Encoding AmpC-type Beta-lactamase," *Gene* 139:93–98 (1994); Jacoby and Medeiros, "More Extended-spectrum Beta-lactamases," *Antimicrob. Agents Chemother.* 35:1697–1704 (1991); Papanicolaou et al., "Novel Plasmid-mediated Beta-lactamase (MIR-1) Conferring Resistance to Oxyimino- and Alpha-methoxy Beta-lactams in Clinical Isolates of *Klebsiella pneumoniae*," *Antimicrob. Agents Chemother.* 34:2200–2209 (1990)). Although Amyes ("Genes and Spectrum: The Theoretical Limits," *Clin. Infect. Dis.* 27 Suppl 1:S21–28) suggests that AmpC β-lactamases presently do not seem efficient enough to cause widespread clinical problems, others are quite concerned that the AmpC β-lactamases constitute a pool from which clinically significant resistant strains may well emerge (see Lindberg and Normark, "Contribution of Chromosomal Beta-lactamases to Beta-lactam Resistance in Enterobacteria," *Rev. Infect. Dis.* 8 Suppl 3:S292–304 (1986); Morosini et al., "An Extended-spectrum AmpC-type Beta-lactamase Obtained by in vitro Antibiotic Selection," *FEMS Microbiol. Lett.* 165:85–90 (1998); Pitout et al., "Antimicrobial Resistance with Focus on Beta-lactam Resistance in Gram-negative Bacilli," *Am. J. Med.* 103: 51–59 (1997)). That concern is exacerbated by the finding that in a clinical isolate of *Enterobacter cloacae*, the AmpC β-lactamase has extended its substrate range to include the oxyimino β-lactams as the result of a tandem duplication of three amino acids (Nukaga et al., "Molecular Evolution of a Class C Beta-lactamase Extending its Substrate Specificity," *J. Biol. Chem.* 270:5729–5735 (1995)(erratum published at *J. Biol. Chem.* 270(36):21428)). More recently, Morosini and colleagues ("An Extended-spectrum AmpC-type Beta-lactamase Obtained by in vitro Antibiotic Selection," *FEMS Microbiol. Lett.* 165:85–90 (1998)) applied direct selection to isolate a mutant of an *Enterobacter cloacae* AmpC β-lactamase in which the activity toward a $4^{th}$ generation cephalosporin had increased 267-fold as the result of a single amino acid replacement.

Together, the facts that mutations to hyper-expression of AmpC occur readily and hyper-expressed ampC β-lactamases (a) already confer resistance to penicillins and $3^{rd}$ generation cephalosporins, (b) are moving onto plasmids, and (c) can easily mutate to significant activity against $4^{th}$ generation cephalosporins suggest that AmpC β-lactamases may very well constitute a potentially serious clinical threat.

The above observations make it clear that new antibiotic resistance can arise when more or less primitive, chromosomal, antibiotic genes are mobilized onto plasmids. Thus, a need exists to identify putative antibiotic resistance genes before they become effective and can cause great damage to the public health. With the genome sequences of literally hundreds of microorganisms now being determined, opportunities are now available to identify those suspected resistance genes, to determine whether they can, in fact, become clinical antibiotic resistance determinants, and to design drugs that can remain effective in the presence of those determinants. What is lacking is a systematic approach for doing so.

The present invention is directed to overcoming the above-identified deficiencies in the art.

SUMMARY OF THE INVENTION

A first aspect of the present invention relates to a method of identifying putative antibiotic resistance genes which includes: isolating a microbial DNA molecule or cDNA which encodes a putative antibiotic resistance protein or polypeptide and determining whether the microbial DNA molecule or cDNA confers resistance against an antibiotic agent.

A second aspect of the present invention relates to a method of identifying putative antibiotic resistance genes which includes: determining whether a microbial DNA molecule confers resistance against an antibiotic agent when the microbial DNA molecule is expressed in its native cell following transformation of the cell and isolating the microbial DNA molecule or cDNA which confers resistance against the antibiotic agent.

A third aspect of the present invention relates to a transposon which includes, in a single DNA molecule: a pair of inverted repeats at opposite ends of a DNA molecule; and a promoter region which is oriented in a manner that affords transcription of coding regions located outside of the transposon sequence following insertion of the transposon into genomic DNA of a host cell, wherein the promoter region initiates transcription using an RNA polymerase native to the host cell. Bacterial host cells transformed with a transposon of the present invention are also disclosed.

The present invention is directed to identifying putative antibiotic resistance genes present in microbial genomes, which putative antibiotic resistance genes do not confer, in their native state, resistance phenotypes to their native hosts. By conducting computer-assisted analyses or in vivo transposon-based detection schemes, it is possible to identify putative antibiotic resistance genes which, when expressed in transgenic host cells, confer an antibiotic resistance phenotype. Each of these schemes offers specific benefits. For example, using computer-assisted analyses of databases, it is possible to identify putative antibiotic resistance genes whose encoded proteins or polypeptides simply lack adequate regulatory control sequences which would otherwise allow them to confer antibiotic resistance, as well as sequences which need to further evolve to confer antibiotic resistance. By way of comparison, the in vitro transposon-based detection scheme allows for identification of putative antibiotic resistance genes which already are capable of conferring some degree antibiotic resistance (i.e., without further evolution) but fail to do so in their native state because of inadequate regulatory control. Either alone or in combination, these two schemes allow for a powerful and systematic process for screening genomes. By identifying these putative antibiotic resistance genes before they naturally arise in nature, i.e., prior to horizontal transfer or other genomic rearrangement or mutation which results in the resistance phenotype, it is possible to develop drugs which will effectively combat the resistance capacity of these putative antibiotic resistance genes. In this fashion, it is possible to identify next generation drugs before natural selection would allow for such drug development to occur.

BRIEF DESCRIPTION OF THE DRAWINGS

FIGS. 2A–B illustrate the map of plasmid pAAC(6')-Iaa (FIG. 2A) and the nucleotide sequence of the AAC(6')-Iaa coding region of *Salmonella enteritidis* serovar *typhimurium* strain LT2 (FIG. 2B, SEQ ID NO: 1).

FIGS. 3A–B illustrate the map (FIG. 3A) and nucleotide sequence (FIG. 3B, SEQ ID No: 2) of a transposon designated MOD3-pTac. The pTac promoter is the complement of bp 133–296 in SEQ ID NO: 2. MOD3-pTac, when inserted into genomic DNA of a host cell, can be used to identify putative, antibiotic resistance genes.

FIGS. 4A–B illustrate the map (FIG. 4A) and nucleotide sequence (FIG. 4B, SEQ ID NO: 3) of a transposon designated GeneHunter<Cam>, which has been prepared by inserting into MOD3-pTac a chloramphenicol resistance gene.

DETAILED DESCRIPTION OF THE INVENTION

Figure 1:
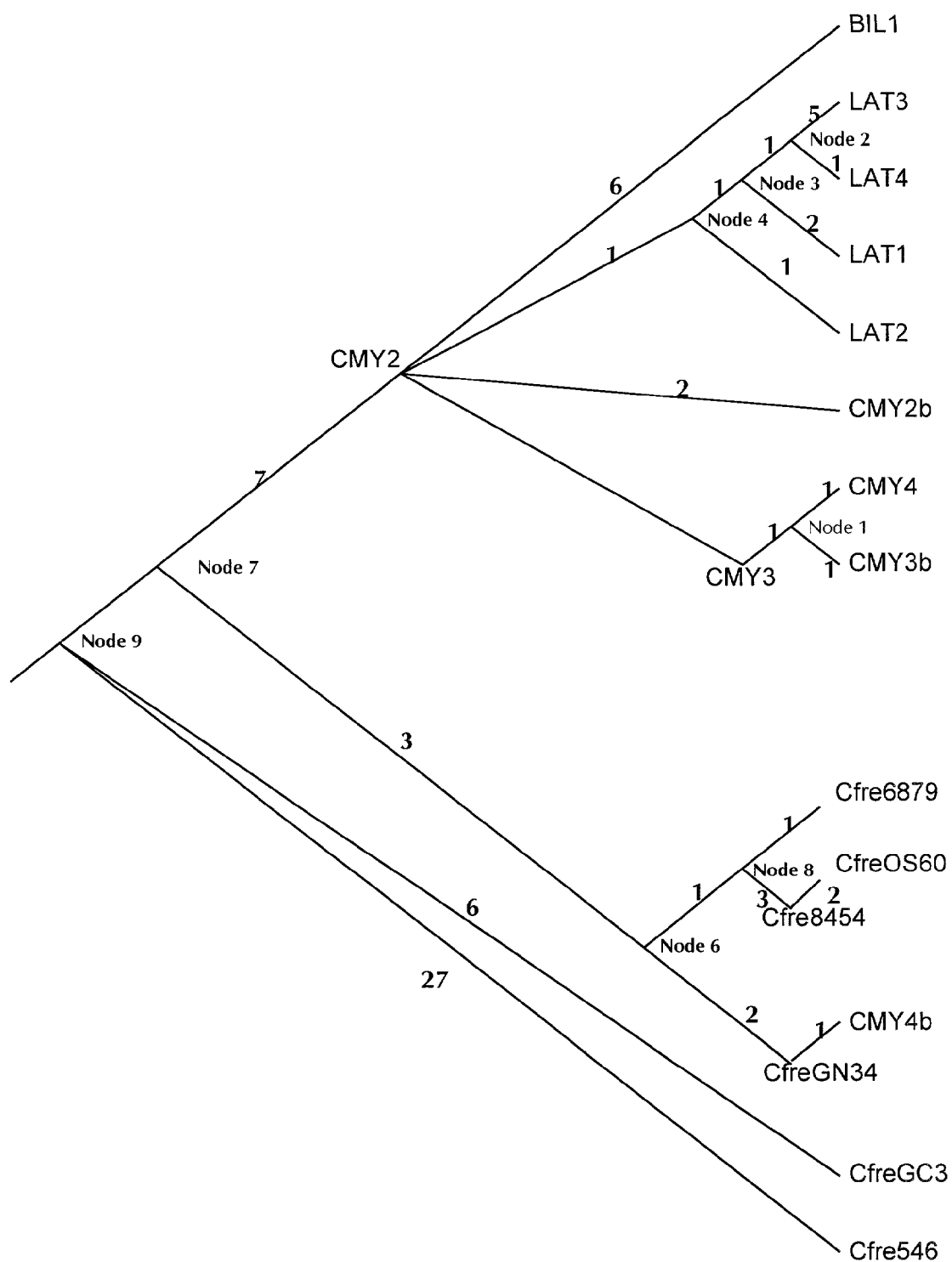
FIG. 1 is phylogenetic tree illustrating the relatedness of *Citrobacter freundii* ampC genes, where majority rule consensus of 500 Baysian Trees was used. Branch lengths are amino acid replacements estimated by Ancestral States program.

The present invention relates to various methods of identifying putative antibiotic resistance genes. By putative antibiotic resistance genes, it is intended that the resistance genes are present in a strain of bacteria, either pathogenic or nonpathogenic, but do not presently confer a resistance phenotype to the bacteria. There may be any one of several reasons for the failure of the putative antibiotic resistance gene to confer a resistance phenotype including, without limitation, (1) failure to be expressed (i.e., in its native state) at levels required for resistance, either as a result of ineffective regulatory sequences (e.g., promoter, enhancer, repressor, etc.) or complete absence thereof; (2) the need for one or more mutations necessary to convert a latent gene into an antibiotic resistance gene; or both.

According to a first embodiment of the present invention, the method of identifying putative antibiotic resistance genes is carried out by first isolating a microbial DNA molecule or cDNA which encodes a putative antibiotic resistance protein or polypeptide and then determining whether the microbial DNA molecule or cDNA confers resistance against an antibiotic agent.

Prior to isolating the microbial DNA molecule or cDNA, the microbial DNA molecule or cDNA is preferably identified from a pool of chromosomally encoded microbial DNA molecules or their corresponding cDNAs. The pool of chromosomally encoded microbial DNA molecules or cDNAs can exist in the form of a collection of genomic fragments or in the form of a database of nucleotide and amino acid sequences which correspond to, respectively, coding regions of microbial genes and the encoded proteins or polypeptides. Thus, the particular approach for identifying the microbial DNA molecule or cDNA depends, at least in part, upon the nature of the pool which is being examined for putative antibiotic resistance genes.

One approach involves the examination of pools which include a collection of genomic fragments obtained, for example, by restriction enzyme treatment with one or more restriction enzymes that can collectively achieve genomic fragments averaging between about 1000 nt and about 5000 nt in length. The genomic fragments can be probed using a nucleic acid (either DNA or RNA) according to known hybridization procedures such as Southern blotting or Northern blotting and subsequently isolated following hybridization. The nucleic acid used for probing the genomic fragments is a nucleic acid which encodes a known antibiotic resistance protein or polypeptide fragment thereof. Thus, depending upon the size of the probe and the stringency of the hybridization and wash conditions, a reasonable degree of certainty can be provided that any genomic fragment which is isolated will code for a putative antibiotic resistance protein or polypeptide fragment thereof. Suitable probe sizes include from about 20 nt in length up to about 300 nt in length, preferably about 25 nt to about 150 nt in length, more preferably about 30 nt to about 100 nt in length. Suitable hybridization conditions will vary depending upon probe length, GC content, and whether RNA or DNA probes are being employed, as is well known in the art. Exemplary hybridization conditions involve incubation of the membrane in a solution which includes 5x-SSC containing 1 g/L sodium laurel sarcosine and denatured probe DNA for 16 hours at about 40–75° C. (typically about 68° C.), followed by two 30 minute washes in 2x-SSC containing 1 g/L sodium dodecyl sulfate and two washes in 0.5x-SSC containing 1 g/L sodium dodecyl sulfate. The temperature of the washes depends upon the desired stringency, ranging from about 40–75° C., but is typically about 68° C. for a moderately stringent wash. (1x-SSC is 8.8 g sodium chloride and 4.4 g sodium acetate per liter in water.)

Once isolated, the genomic fragment hybridizing to a nucleic acid probe can be sequenced to identify whether it contains a full coding sequence (i.e., start and stop codons for a putative antibiotic resistance gene) or only a partial coding sequence. If a full coding sequence is identified, then the microbial DNA molecule or cDNA can tested to determine whether it can confer antibiotic resistance (discussed infra). Alternatively, if a less than full length coding sequence is identified, the partial sequence can be utilized to develop primers designed to amplify the upstream or downstream sequences needed to complete the entire coding sequence. Following, one or more rounds of polymerase chain reaction ("PCR") amplification and sequencing of PCR products, the full length coding sequence can be identified.

Another approach involves the examination of pools of amino acid sequences or nucleotide sequences which are present in one or more electronic databases, such as Genbank, EMBL, etc. In this approach, identifying the microbial DNA molecule or cDNA is carried out using computer-assisted analysis of electronic sequence databases. Using known antibiotic resistance genes and their encoded proteins or polypeptides, the corresponding nucleotide and/or amino acid sequences are used to search the electronic database to identify chromosomally encoded microbial DNA molecules or their corresponding cDNAs. This can be achieved in any number of ways given the availability of a wide variety of computer-assisted analysis tools.

Suitable computer-assisted analysis tools include, without limitation, BLAST (Altschul et al., "Basic Local Alignment Search Tool," *J. Mol. Biol.* 215(3):403–410 (1990), which is hereby incorporated by reference in its entirety), Reverse Position Specific BLAST (Altschul et al., "Gapped BLAST and PSI-BLAST: A New Generation of Protein Database Search Programs," *Nucleic Acids Res.* 25:3389–3402 (1997), which is hereby incorporated by reference in its entirety), FASTA (Pearson and Lipman, "Improved Tools for Biological Sequence Analysis," *Proc. Natl. Acad. Sci. USA* 85:2444–2448 (1988); Pearson, "Rapid and Sensitive Sequence Comparison with FASTP and FASTA," *Methods in Enzymology* 183:63–98 (1990), each of which is hereby incorporated by reference in its entirety), SCANPS (Barton, "Computer Speed and Sequence Comparison," *Science* 257: 1609 (1992); Cuff and Barton, "Application of Multiple Sequence Alignment Profiles to Improve Protein Secondary Structure Prediction," *PROTEINS: Structure Function and Genetics* 40:502–511 (2000), each of which is hereby incorporated by reference in its entirety). Other computer-assisted sequence search tools can also be employed, either alone or in combination with the above-listed search tools.

A first database search routine involves comparing the amino acid sequence of a known antibiotic resistance protein or polypeptide against a database of microbial protein or polypeptide sequences under conditions effective to obtain the amino acid sequence of the putative antibiotic resistance protein or polypeptide, wherein the obtained amino acid is paired in the database with nucleotide sequence of the microbial DNA molecule or cDNA.

Exemplary antibiotic resistance genes include, without limitation, the katG, rpoB, and rpsL genes of *Mycobacterium tuberculosis* (C.D.C., "Outbreak of Multidrug-resistant Tuberculosis—Texas, California, and Pennsylvania," MMWR 39:369–372 (1990); C.D.C., "Nosocomial Transmission of Multidrug-resistant Tuberculosis Among HIV-infected Persons—Florida and New York 1988–1991," MMWR 40:585–591 (1991); C.D.C., "Transmission of Multidrug-resistant Tuberculosis from an HIV-positive Client in a Residential Substance Abuse Treatment Facility—Michigan," MMWR 40:129–131 (1991), each of which is hereby incorporated by reference in its entirety); ampC genes of Gram negative bacteria, including both the *Enterobacteriaceae* and *Pseudomonas* species (Lindberg et al., "Contribution of Chromosomal beta-lactamases to beta-lactam Resistance in Enterobacteria," *Rev. Infect. Dis.* 8 Suppl 3:S292–304 (1986); Morosini et al., "An Extended-spectrum AmpC-type beta-lactamase Obtained by in vitro Antibiotic Selection," *FEMS Microbiol. Lett.* 165:85–90 (1998); and Pitout et al., "Antimicrobial Resistance with Focus on beta-lactam Resistance in Gram-negative Bacilli," *Am. J. Med.* 103:51–59 (1997), each of which is hereby incorporated by reference in its entirety); TEM/SHV β-lactamases and their extended spectrum derivatives (reviewed in Jacoby, "Genetics of Extended-spectrum Beta-lactamases," *Eur. J. Clin. Microbiol. Infect. Dis.* 13 Suppl 1:S2–11 (1994), which is hereby incorporated by reference in its entirety); aminoglycoside resistance genes such as aminoglycoside kinases, aminoglycoside acetylases, and aminoglycoside adenylases (reviewed in Shaw et al., "Molecular Genetics of Aminoglycoside Resistance Genes and Familial Relationships of the Aminoglycoside-modifying Enzymes," *Microbiol. Rev.* 57(1):138–163 (1993), which is hereby incorporated by reference in its entirety); fluoroquinolone resistance genes, including mexA, mexB, and oprM of *Pseudomonas aeruginosa* (Poole et al., "Cloning and Sequence Analysis of an EnvCD Homologue in *Pseudomonas aeruginosa*: Regulation by Iron and Possible Involvement in the Secretion of the Siderophore Pyoverdine," *Mol. Microbiol.* 10(3):529–544 (1993); Poole et al., "Multiple Antibiotic Resistance in *Pseudomonas aeruginosa*: Evidence for Involvement of an Efflux Operon," *J. Bacteriol.* 175(22):7363–7372 (1993), each of which is hereby incorporated by reference in its entirety); macrolide resistance genes, including methylases (ermA), ATP binding transporters (carA), major facilitators (lmrA), esterases (ereA), hydrolases (vgbA), transferases (InvA), and phosphorylases (mphA) (reviewed in Roberts et al., "Nomenclature for Macrolide and Macrolide-Lincosamide-Streptogramin B Resistance Determinants," *Antimicrob. Agents Chemother.* 43(12):2823–2830 (1999), which is hereby incorporated by reference in its entirety); tetracycline and tetracycline-derivative resistance genes, including efflux (tetA) and ribosomal protection (tetM) proteins (reviewed in Levy et al., "Nomenclature for New Tetracycline Resistance Determinants," *Antimicrob. Agents Chemother.* 43(6):1523–1524 (1999), which is hereby incorporated by reference in its entirety); chloramphenicol and chloramphenicol-derivative resistance genes including pp-cat of *Pasteurella piscicida* (Kim and Aoki, "The Structure of the Chloramphenicol Resistance Gene on a Transferable R Plasmid from the Fish Pathogen, *Pasteurella piscicida*," *Microbiol. Immunol.* 37(9):705–712 (1993), which is hereby incorporated by reference in its entirety); glycopeptide resistance genes including vanA, vanH, vanR, vanS, vanX, vanY, and vanZ of *Bacillus circulans* (reviewed in Ligozzi et al., "vanA Gene Cluster in a Vancomycin-resistant Clinical Isolate of *Bacillus circulans*," *Antimicrob. Agents Chemother.* 42(8): 2055–2059 (1998), which is hereby incorporated by reference in its entirety); and sulfonamide/trimethoprim resistance genes, including folC, folE, folP, folB, and folK of *Streptococcus pyogenes* (Swedberg et al., "Sulfonamide Resistance in *Streptococcus pyogenes* is Associated with Differences in the Amino Acid Sequence of its Chromosomal Dihydropteroate Synthase," *Antimicrob. Agents Chemother.* 42 (5):1062–1067 (1998), which is hereby incorporated by reference in its entirety).

When utilizing amino acid sequences as the database query, the comparison of amino acid sequences (i.e., between the known antibiotic resistance protein or polypeptide and the putative antibiotic resistance protein or polypeptide) can be carried out by assessing the identity and/or similarity between the amino acid sequences. Alternatively, the comparison of amino acid sequences can be carried out by assessing whether the putative antibiotic resistance protein or polypeptide includes one or more functional domains which are conserved between (i.e., present in and high in amino acid identity or similarity) both the putative antibiotic resistance protein or polypeptide and the known antibiotic resistance protein or polypeptide. The conserved functional domain is preferably one which is conserved among a number of known antibiotic resistance genes.

The putative antibiotic resistance protein or polypeptide should have sufficient amino acid identity with the known antibiotic resistance protein(s) whose nucleotide or amino acid sequences were used for their identification. Depending on whether or not a particular putative antibiotic resistance protein or polypeptide has the same substrate specificity as the antibiotic resistance protein or polypeptide whose sequence was used to probe a database, a greater or lesser degree of sequence identity/similarity can be expected. Where the same specificity is expected, suitable amino acid identity is at least about 30 percent identity, preferably at least about 40 percent identity, more preferably at least about 50 percent identity. Where the putative antibiotic resistance protein has less than about 50 percent amino acid identity, then the degree of amino acid similarity (i.e., based on conserved substitutions) should be at least about 50 percent, preferably at least about 60 percent similarity, more preferably at least about 70 percent similarity. Where a different specificity is expected, suitable amino acid identity is typically at least about 25 percent identity but not more than about 50 percent identity, preferably between about 30 percent identity and 45 percent identity.

Amino acid similarity can be determined based on whether a changed amino acid residue (in the putative antibiotic resistance protein as compared to the known antibiotic resistance protein) belongs to the same grouping of amino acids having a particular size or characteristic. These are considered conserved substitutions. Non-conserved substitutions, in contrast, involve changes where the changed amino acid residue (in the putative antibiotic resistance protein as compared to the known antibiotic resistance protein) belongs to a different grouping of amino acids. Generally, conservative changes lead to minimal change in the structure and function of the resulting protein, whereas non-conservative changes more likely lead to alterations in the structure, activity, or function of the resulting protein. For computer-assisted sequence analysis tools designed to analyze protein or polypeptide sequences, they typically utilize one or more amino acid groupings to calculate similarity.

One example of various groupings of amino acids is as follows: (1) amino acids with nonpolar R groups (alanine, valine, leucine, isoleucine, proline, phenylalanine, tryptophan, and methionine); (2) amino acids with uncharged polar R groups (glycine, serine, threonine, cysteine, tyrosine, asparagine, and glutamine); (3) amino acids with charged polar R groups, i.e., negatively charged at pH 6.0 (aspartic acid and glutamic acid); (4) basic amino acids, i.e., positively charged at pH 6.0 (lysine, arginine, histidine); (5) amino acids with phenyl groups (phenylalanine, tryptophan, and tyrosine).

Another grouping may be according to molecular weight, i.e., based on the size of R groups as follows: glycine, 75; alanine, 89; serine, 105; proline, 115; valine, 117; threonine, 119; cysteine, 121; leucine, 131; isoleucine, 131; asparagine, 132; aspartic acid, 133; glutamine, 146; lysine, 146; glutamic acid, 147; methionine, 149; histidine (at pH 6.0), 155; phenylalanine, 165; arginine, 174; tyrosine, 181; and tryptophan, 204.

A second database search routine involves comparing the nucleotide sequence coding for a known antibiotic resistance protein or polypeptide against a database of microbial nucleotide sequences under conditions effective to obtain a nucleotide sequence of the microbial DNA molecule or cDNA which codes for the putative antibiotic resistance protein or polypeptide. The nucleotide sequence for the known antibiotic resistance proteins or polypeptides can be one which encodes an above-listed antibiotic resistance protein or polypeptide.

When utilizing nucleotide sequences as the database query, the comparison of nucleotide sequences (i.e., between the known antibiotic resistance gene and the putative antibiotic resistance gene) can be carried out by assessing whether the nucleotide sequence of the microbial DNA molecule or cDNA is similar to the nucleotide sequence coding for the known antibiotic resistance protein or polypeptide. By similar, it is intended that the nucleotide sequences have at least about 60 percent identity over about 80 percent of the length of the gene, preferably at least about 70 percent identity over about 90 percent of the length of the gene. The nucleotide coding sequence for the putative antibiotic resistance protein or polypeptide may or may not have a high degree of identity with the nucleotide sequence for the known antibiotic resistance protein(s), depending on the degree to which degenerate substitutions are present. Degenerate substitutions in the nucleic acid produce different codons which code for the same amino acid residue and, therefore, have no effect on the overall protein sequence. Typically, though, highly conserved regions (i.e., of high identity) will exist even in the nucleotide sequences. As noted above with regard to substrate specificity of putative and known antibiotic resistance proteins or polypeptide, the same should also hold true for the encoding nucleotide sequences thereof (i.e., lower nucleotide identity when the encoded putative antibiotic resistance protein or polypeptide would be expected to have a different substrate specificity and a higher nucleotide identity when the encoded putative antibiotic resistance protein or polypeptide would be expected to have the same substrate specificity).

Having identified the microbial DNA molecule or cDNA which encodes a putative antibiotic resistance protein, the DNA molecule can be isolated using conventional molecular techniques, including PCR using appropriate forward and reverse primers to amplify the microbial DNA molecule or cDNA, followed by electrophoresis to separate the desired DNA molecule.

To determine whether the identified putative antibiotic resistance protein or polypeptide, in fact, confers antibiotic resistance to its host, the microbial DNA molecule or cDNA is used to transform a host cell under conditions effective to express the putative antibiotic resistance protein or polypeptide. Basically, transformants (which also contain a selection marker) are then selected on a suitable, selective growth medium and the transformants are transferred to a growth medium including an antibiotic agent (or a plurality of antibiotic agents), wherein proliferation of host cells indicates antibiotic resistance conferred by expression of the putative antibiotic resistance protein or polypeptide.

The DNA molecule encoding the putative antibiotic resistance protein can be incorporated in cells using conventional recombinant DNA technology. Generally, this involves inserting the DNA molecule into an expression system to which the DNA molecule is heterologous (i.e., not normally present). The heterologous DNA molecule is inserted into the expression system or vector in sense orientation and correct reading frame. Depending on the vector, the DNA molecule can be ligated to appropriate regulatory sequences either prior to its insertion into the vector (i.e., as a chimeric gene) or at the time of its insertion (i.e., thereby forming the chimeric gene). The DNA molecule can be cloned into the vector using standard cloning procedures in the art, as described by Maniatis et al., *Molecular Cloning: A Laboratory Manual*, Cold Springs Laboratory, Cold Springs Harbor, N.Y. (1982), which is hereby incorporated by reference in its entirety.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Recombinant genes may also be introduced into viruses, such as vaccinia virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene (La Jolla, Calif.), which is hereby incorporated by reference in its entirety), pQE, pIH821, pGEX, pET series (see Studier et. al., "Use of T7 RNA Polymerase to Direct Expression of Cloned Genes," *Gene Expression Technology*, vol. 185 (1990), which is hereby incorporated by reference in its entirety), and any derivatives thereof. Suitable vectors are continually being developed and identified.

Recombinant molecules can be introduced into host cells via transformation, transduction, conjugation, mobilization, or electroporation.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria or transformed via particle bombardment (i.e. biolistics). The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA ("mRNA") translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters typically are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference in its entirety.

Promoters vary in their "strength" (i.e., their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno ("SD") sequence about 7–9 bases 5' to the initiation codon ("ATG") to provide a ribosome binding site. Thus, any SD-ATG combination that can be utilized by host cell ribosomes may be employed. Such combinations include, but are not limited to, the SD-ATG combination from the cro gene or the N gene of coliphage lambda, or from the *E. Coli* tryptophan E, D, C, B or A genes. Additionally, any SD-ATG combination produced by recombinant DNA or other techniques involving incorporation of synthetic nucleotides may be used.

Once the DNA molecules encoding the putative antibiotic resistance proteins, as described above, have been cloned into an expression system, they are ready to be incorporated into a host cell. Such incorporation can be carried out by the various forms of transformation noted above, depending upon the vector/host cell system. Suitable host cells include, but are not limited to, bacteria, virus, yeast, mammalian cells, insect, plant, and the like.

The transformed hosts of the invention may be cultured under protein producing conditions according to any of the methods which are known to those skilled in the art. The transformed hosts are grown on a selection media which includes one or more antibiotic agents, e.g., one antibiotic agent which inhibits growth of non-transformed cells and a second antibiotic agent which is used to select for resistance of transformants expressing the putative antibiotic resistance gene. Alternatively, transformants first can be proliferated on a selection media which selects against non-transformants and then transformants can be serially tested by growing them in a plurality of different selection media (each including a different antibiotic agent or combination thereof). Growth of transformants on the selection media including an antibiotic agent used for screening purposes confirms that the putative antibiotic resistance gene is, in fact, an antibiotic resistance gene.

When the transformation and selection procedures described above indicate that the putative antibiotic resistance protein or polypeptide does, in fact, confer antibiotic resistance, the mutagenic potential of the antibiotic resistance protein or polypeptide can be assessed using the procedures described in co-pending U.S. patent application Ser. No. 09/640,882 to Hall, filed Aug. 18, 2000, which is hereby incorporated by reference in its entirety.

Basically, the newly-defined antibiotic resistance gene is first mutated to prepare a mutant antibiotic resistance gene that contains a plurality of mutations (i.e., either in the coding region or regulatory region) such that expression of the mutant antibiotic resistance gene confers to its host organism enhanced resistance against conventional antibiotic treatments. Once the mutant antibiotic resistance gene is obtained, it is then determined whether such a mutant antibiotic resistance gene is capable of evolving by a series of individual mutation events. This is determined by replicating discrete mutation events and then selecting for any enhanced activity (i.e., resistance) against conventional antibiotic treatments. This process is repeated by screening singly mutated antibiotic resistance genes, then doubly mutated antibiotic resistance genes, and so on, until it is determined whether the first obtained mutant antibiotic resistance gene is or is not likely to evolve under environmental selection. When it is determined that such a mutant antibiotic resistance gene or a multiply mutated antibiotic resistance gene is capable of evolving (i.e., in response to conventional antibiotics), then such a mutant resistant gene or multiply mutated resistance gene can be used to screen for next generation drugs.

In this fashion, it is possible to identify next generation drugs before natural selection would allow for such drug development to occur. Moreover, it is possible to determine whether such next generation drugs are likely to provide long-lasting therapeutic treatment against organisms possessing mutant resistance genes. This determination can be made by assessing the number of discrete mutational events which would be required for an individual to overcome the effects of treatment by such a next generation drug. The greater the number of discrete mutational events which would be required to overcome the efficacy of such a drug, then the more likely that such a drug would have longer-lasting efficacy. This would enable drug manufacturers the opportunity to assess the potential profitability of one drug versus another.

This same procedure (described in co-pending U.S. patent application Ser. No. 09/640,882 to Hall, filed Aug. 18, 2000, which is hereby incorporated by reference in its entirety) can also be performed when the transformation and selection procedures described above indicate that the putative antibiotic resistance protein or polypeptide does not confer antibiotic resistance. In this case, the mutagenic potential of the putative antibiotic resistance protein or polypeptide can be assessed to determine whether the putative antibiotic resistance protein or polypeptide can evolve, through one or more mutation events, to confer an antibiotic resistance phenotype.

According to a second embodiment of the present invention, the method of identifying putative antibiotic resistance genes is carried out by first determining whether a microbial DNA molecule confers resistance against an antibiotic agent when the microbial DNA is expressed in its native cell following transformation of the cell and then isolating the microbial DNA molecule or cDNA which confers resistance against the antibiotic agent. In this embodiment, an in vivo scheme is employed to determine whether a microbe includes in its genome a putative antibiotic resistance gene encoding an antibiotic resistance protein or polypeptide, followed by in vitro isolation and identification procedures (e.g., PCR amplification and sequencing on automated sequencing apparatus).

This in vivo scheme for determining whether a microbial DNA molecule or cDNA confers antibiotic resistance utilizes the capabilities of a transposon. Basically, a transposon of the present invention is introduced into the genomic DNA of a host cell and then transformed host cells are grown on a selection media which includes an antibiotic agent, whereby proliferation of host cells indicates that a microbial DNA molecule is expressed and confers resistance against the antibiotic agent.

At a minimum, a transposon of the present invention includes, in a single DNA molecule, a pair of inverted repeats at opposite ends of a DNA molecule and a promoter region which is oriented in a manner that affords transcription of coding regions located outside of the transposon sequence following insertion of the transposon into genomic DNA of a host cell, wherein the promoter region initiates transcription using an RNA polymerase native to the host cell. Preferably, the transposon also includes one or more restriction sites located between the pair of inverted repeats, an origin of replication (suitable for the cells being transformed) located between the pair of inverted repeats, and a selection marker located between the pair of inverted repeats. The transposon can also include one or more primer annealing sites which can later be used to amplify and/or sequence a nucleic acid molecule encoding an antibiotic resistance protein or polypeptide (see infra).

A transposon of this type can be constructed using a MOD-3 transposon that is contained within the pMOD-3 plasmid available from Epicentre Technologies (Madison, Wis.). The MOD-3 transposon includes a DNA sequence with hyperactive 19 bp inverted repeats, termed mosaic ends or outer elements, at each end of the sequence. The outer elements are specifically recognized by EZ::TN Transposase, which is also available from Epicentre Technologies. Between the outer elements is a multiple cloning site that includes sites for several common restriction enzymes, a RK6γ origin of replication (RK6 Ori), PCR primer annealing sites, and sequencing primer annealing sites.

According to one embodiment, a transposon designated MOD3-pTac is illustrated in FIGS. 3A–B. MOD3-pTac has been prepared by introducing a highly efficient pTac promoter into the MOD-3 transposon in an orientation such that transcription regulated by pTac occurs outward from one end of the transposon.

Figure 4A:
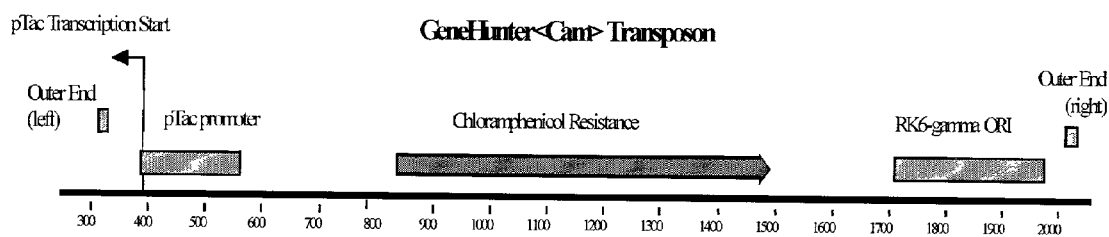

According to another embodiment, a transposon designated GeneHunter<Cam> is illustrated in FIGS. 4A–B. GeneHunter<Cam> has been prepared by inserting into MOD3-pTac a chloramphenicol resistance gene (i.e., including its own promoter and transcription termination sequence) which can be used as a selection marker to identify transformants in which the GeneHunter<Cam> has been inserted. Other resistance genes including, without limitation, kanamycin resistance gene, streptomycin resistance gene, and cefotaxime resistance gene can also be inserted into MOD3-pTac to prepare alternative transposon constructs related to GeneHunter<Cam>.

The transposons of the present invention can be utilized in combination with EZ::TN Transposase (Epicentre Technologies) in accordance with the manufacturer's instructions. Basically, a transposon such as GeneHunter<Cam> can be combined with EZ::TN Transposase (Epicentre) in the absence of magnesium, allowing a complex between the transposase and the outer elements of the transposon to be formed. When the transposon/transposase complex is mixed with target DNA (either in vivo or in vitro) in the presence of magnesium, transposition occurs and the transposon is inserted at random sites into the target DNA molecule. In vivo transposition is accomplished by introducing the transposon/transposase complex into living target cells by electroporation, in which case intracellular magnesium initiates transposition. In vitro transposition is accomplished by mixing the transposon/transposase complex with genomic DNA of the target organism in the presence of magnesium according to manufacturer's instructions.

In the case of in vivo transposition, multiple transformants will be prepared, i.e., at least about $10^5$, preferably at least about $10^6$. Thereafter, transformed hosts may be cultured under protein producing conditions according to any of the methods which are known to those skilled in the art. According to one approach, both transformed and non-transformed hosts are grown on a selection medium which includes one or more antibiotic agents, e.g., one antibiotic agent which inhibits growth of non-transformed cells (such as chloramphenicol for GeneHunter<Cam>) and a second antibiotic agent which is used to select for resistance of transformants expressing the putative antibiotic resistance gene. Alternatively, transformants first can be proliferated on a selection medium which selects against non-transformants (such as chloramphenicol-containing media for GeneHunter<Cam>) and then transformants can be serially tested by growing them in a plurality of different selection media (each including a different antibiotic agent or combination thereof). Regardless of the approach utilized, growth of transformants on the selection medium including an antibiotic agent used for screening purposes confirms that the transposon has inserted into the genome upstream of a putative antibiotic resistance gene which, absent the pTac promoter, would not normally be expressed in a manner sufficient to confer a resistance phenotype.

Regardless of the embodiment utilized for identifying the microbial DNA molecule or cDNA which encodes a putative antibiotic resistance protein or polypeptide and determining whether the microbial DNA molecule or cDNA confers resistance against an antibiotic agent, resistance against a number of antibiotic resistance agents can be tested including those described above.

The mode by which resistance can be conferred to a transformed host organism is not important; it is merely necessary for such a gene to confer a selective advantage, such as drug resistance. For example, resistance genes can be generally assigned to five different types of resistance genes based upon the mode by which they confer resistance to their host organisms. One type of resistance gene is characterized by expression products (of the resistance gene) which destroy a therapeutic drug. Without being bound thereby, an example of this type of resistance gene is the ampicillin resistance gene of *E. coli* plasmid pBR322 (Sutcliffe, "Nucleotide Sequence of the Ampicillin Resistance Gene of *Escherichia coli* plasmid pBR322," *Proc. Natl. Acad. Sci. USA* 75:3737–3741 (1978), which is hereby incorporated by reference in its entirety). A second type of resistance gene is characterized by expression products which effectively pump the drug out of the host cell such that the drug cannot effectively compromise host organism survival. Without being bound thereby, an example of this type of resistance gene is the tetA gene of plasmid RP1, which imparts resistance to tetracycline (Water et al., "The Tetracycline Resistance Determinants of RP1 and Tn1721: Nucleotide Sequence Analysis," *Nucleic Acids Res.* 11(17): 6089–6105 (1983), which is hereby incorporated by reference in its entirety). A third type of resistance gene is characterized by expression products which modify a drug to render it ineffective (i.e., via phosphorylation, acetylation, adenylation, etc.). Without being bound thereby, an example of this type of resistance gene is the aph(32)-Ib gene of plasmid RP4 which imparts resistance to aminoglycosides (Pansegrau et al., "Nucleotide Sequence of the Kanamycin Resistance Determinant of Plasmid RP4: Homology to Other Aminoglycoside 32-Phosphotransferases," *Plasmid* 18:193–204 (1987), which is hereby incorporated by reference in its entirety). A fourth type of resistance gene is characterized by expression products which mutate frequently, thereby modifying the drug target to diminish the ability of such a drug to compromise host organism survival. Without being bound thereby, an example of this type of resistance is the rapid development of variant proteases by RNA viruses, such as HIV-1 and HIV-2, which can avoid disruption by conventional protease inhibitors (Condra et al., "In vivo Emergence of HIV-1 Variants Resistant to Multiple Protease Inhibitors," *Nature* 374:569–571 (1995), which is hereby incorporated by reference in its entirety). A fifth type of resistance gene is characterized by overproduction of target enzymes that are no longer sensitive to the antibiotic. Without being bound thereby, examples include acquisition of a plasmid-borne dihydropteroate synthase that is not sensitive to inhibition by sulfonamides and Tn4003-borne dihydrofolate reductase that is not inhibited by trimethoprim, both of which are involved in folic acid biosynthesis. Although the two drugs are often used in combination, resistance to the drug combination is now common (Widdowson et al., "Molecular Mechanisms of Resistance to Commonly Used Non-betalactam Drugs in *Streptococcus pneumoniae*," *Semin. Respir. Infect.* 14(3):255–268 (1999), which is hereby incorporated by reference in its entirety).

After determining that a particular transformant does, in fact, contain an antibiotic resistance gene, primer annealing sites in the transposon can be utilized either for PCR amplification or sequencing of the genomic region immediately downstream of the promoter which is present in the transposon of the present invention. Ultimately, the downstream coding sequence of the newly discovered antibiotic resistance gene can be obtained either from chromosomal gene fragments or PCR amplified cDNA fragments.

Having confirmed that microbial DNA confers an antibiotic resistance phenotype when expressed and having isolated the microbial DNA molecule or cDNA which encodes an antibiotic resistance protein or polypeptide, the mutagenic potential of the antibiotic resistance protein or polypeptide can be assessed using the procedures described in co-pending U.S. patent application Ser. No. 09/640,882 to Hall, filed Aug. 18, 2000, which is hereby incorporated by reference in its entirety.

Basically, the newly-defined antibiotic resistance gene is first mutated to prepare a mutant antibiotic resistance gene that contains a plurality of mutations (i.e., either in the coding region or regulatory region) such that expression of the mutant antibiotic resistance gene confers to its host organism enhanced resistance against conventional antibiotic treatments. Once the mutant antibiotic resistance gene is obtained, it is then determined whether such a mutant antibiotic resistance gene is capable of evolving by a series of individual mutation events. This is determined by replicating discrete mutation events and then selecting for any enhanced activity (i.e., resistance) against conventional antibiotic treatments. This process is repeated by screening singly mutated antibiotic resistance genes, then doubly mutated antibiotic resistance genes, and so on, until it is determined whether the first obtained mutant antibiotic resistance gene is or is not likely to evolve under environmental selection. When it is determined that such a mutant antibiotic resistance gene or a multiply mutated antibiotic resistance gene is capable of evolving (i.e., in response to conventional antibiotics), then such a mutant resistant gene or multiply mutated resistance gene can be used to screen for next generation drugs.

EXAMPLES

The following examples are provided to illustrate embodiments of the present invention but are by no means intended to limit its scope.

Example 1

Evidence for the Importance of Primitive, Chromosomally Located, Potential Resistance Genes

*E. coli* K12 ampC

The ampC gene of *E. coli*K12 is so poorly expressed that deletion of that gene has no effect at all on resistance to β-lactamase antibiotics. Yet when that same gene is cloned into a plasmid and expressed under the control of an effective promoter, it confers clinical resistance to three important drugs: ampicillin, cephalothin, and cefuroxime (Lindberg and Normark, "Contribution of Chromosomal Beta-lactamases to Beta-lactam Resistance in Enterobacteria," *Rev. Infect. Dis.* 8 Suppl 3:S292–304 (1986), which is hereby incorporated by reference in its entirety). *E coli*K12 was isolated in the mid-1920's, thus its ampC gene did not evolve that level of resistance in response to selection from antibiotics in clinical use (i.e., it was already predisposed to confer resistance). In addition, as the result of two or three laboratory-induced mutations, that gene can evolve further to confer resistance to four additional β-lactam antibiotics: pipericillin, temocillin, ceftazidime, and aztreonam (see U.S. patent application Ser. No. 09/640,882 to Hall, filed Aug. 18, 2000, which is hereby incorporated by reference in its entirety). Thus, the *E. coli* ampC gene is a primitive β-lactamase gene that is capable of moving onto a plasmid and then evolving further to provide clinical resistance to many important drugs.

Citrobacter freundii ampC

The plasmid-borne ampC genes shown in Table 1 (below) have been cloned into a common vector to ensure that all genes are expressed at the same level. Those genes, designated CMY-2, CMY-3b, LAT-1, LAT-2, LAT-3, and LAT-4 all confer clinical resistance to ampicillin, temocillin, pipericillin, cephalothin, cefuroxime, cefotaxime, ceftazidime, and (except for CMY2) to aztreonam (Table 1). That is completely expected because those genes were isolated from clinical samples and identified on the basis of conferring resistance to clinical drugs. ampC genes from two strains of Citrobacter freundii that were isolated in the 1920's, in the pre-antibiotic era, were also cloned into the same vector. Those "ancient" ampC genes, without any additional mutations, confer resistance to the same set of drugs (except the Cfre8454 does not confer clinical resistance to ceftazidime) and at essentially the same level as the plasmid-borne genes that have been subjected to selection for drug resistance.

TABLE 1

Minimum Inhibitory Concentrations (MICs) Conferred by β-lactamase Genes

| | | | Citrobacter freundii ampC genes | | | | | | |
|---|---|---|---|---|---|---|---|---|---|
| Drug | Clin. | No Plasmid | CMY2 | CMY3b | LAT1 | LAT2 | LAT3 | LAT4 | Cfre 6879 | Cfre 8454 |
| Ampicillin | 32 | 2 | 1024 | 1024 | 1024 | 2048 | 1024 | 1024 | 1024 | 2048 |
| Pipericillin | 128 | 2 | 256 | 128 | 128 | 256 | 512 | 512 | 512 | 512 |
| Temocillin | 32 | 4 | 32 | 32 | 64 | 32 | 64 | 64 | 32 | 32 |
| Cephalothin | 32 | 4 | 1024 | 2048 | 4096 | 4096 | 2048 | 4096 | 1024 | 2048 |
| Cefuroxime | 32 | 8 | 256 | 1024 | 2048 | 256 | 1024 | 2048 | 512 | 512 |
| Cefotaxime | 64 | 0.125 | 64 | 64 | 64 | 64 | 128 | 256 | 128 | 128 |
| Ceftazidime | 32 | 0.25 | 128 | 256 | 256 | 256 | 256 | 256 | 512 | 8 |
| Aztreonam | 32 | 0.125 | 16 | 128 | 256 | 64 | 64 | 128 | 256 | 128 |

Clin. = the MIC for clinical resistance.
Cfre6879 and Cfre8454 are ampC genes from organisms isolated in the 1920's, in the pre-antibiotic era.

It is therefore possible to conclude that Citrobacter freundii chromosomal ampC genes were primed and ready to become effective clinical resistance determinants simply by moving onto a plasmid. In other words, Citrobacter freundii was a reservoir of a resistance problem waiting to happen. It is quite possible, therefore, that it was the Citrobacter rather than the E. coli ampC gene that actually migrated successfully onto plasmids, simply because the Citrobacter gene was already a more effective β-lactamase.

Example 2

Computer-Assisted Identification of *Salmonella enteritidis* Serovar *typhimurium* Gene and Measure of its Mutagenic Potential The aminogylcoside N6'-acetyltransferase Ic protein of *Serratia marcescens* (AAC(6')-Ic) (Genbank Accession Nos. AAA26549 and M94066, each of which is hereby incorporated by reference in its entirety) was used to search the NCBI database of complete and incomplete microbial genomes. A sequence in the incompletely sequenced genome of *Salmonella enteritidis* serovar *typhimurium* strain LT2 was identified that encodes a protein that is 51% identical and 66% similar to the *S. marcescens* AAC(6')-IC protein. Alignment of the two nucleotide sequences showed no significant similarity.

AAC(6')-I family aminogylcoside acetyltransferases tend to confer resistance to the aminoglycosides kanamycin, tobramycin, gentamycin, and amikacin. Table 2 (below) shows that *Salmonella enteritidis* serovar *typhimurium* strain LT2 is sensitive to each of those drugs.

TABLE 2

Antibiotic Resistance of Native and Transgenic Host Cells Expressing AAC(6')-Iaa

| | Minimum Inhibitory Concentration (μg/ml) | | | |
|---|---|---|---|---|
| | Tobramycin | Kanamycin | Gentamycin | Amikacin |
| *S. enteritidis* serovar *typhimurium* LT2 | 4 | 4 | 2 | 4 |
| DH5α-E/pACSE2 | 0.25 | 0.125 | 0.25 | 0.25 |
| DH5α-E/ pAAC(6')-Iaa | 16 | 32 | 0.5 | 8 |
| Clinical Resistance | 8 | 25 | 8 | 32 |

The putative AAC(6') aminoglycoside N6'-acetyltransferase gene from *Salmonella enteritidis* serovar *typhimurium* strain LT2, designated AAC(6')-Iaa, was amplified by PCR and cloned into the expression vector pACSE2 (U.S. patent application Ser. No. 09/640,882 to Hall, filed Aug. 18, 2000, which is hereby incorporated by reference in its entirety). The resulting plasmid was designated pAAC(6')-Iaa (FIG. 2A). The sequence of the AAC(6')-Iaa coding region was determined by automated DNA sequencing and was confirmed to be identical to the sequence obtained from the incomplete genome sequence database (FIG. 2B).

When transformed into *E. coli* strain DH5α-E, plasmid pAAC(6')-Iaa conferred resistance to tobramycin and to kanamycin, but not to gentamycin or amikacin (Table 2 above).

The evidence above shows that sequence homology searching can be used to identify potential antibiotic resistance genes in the chromosomes of antibiotic sensitive organisms, clone and express those genes, and demonstrate that the genes do, in fact, encode functional resistance proteins.

Mutagenic PCR was used to predict whether the AAC (6')-Iaa gene has the potential to evolve resistance to gentamycin or amikacin, or to provide increased resistance to tobramycin or kanamycin. The GeneMorph kit from Stratagene was used according to manufacturer's instructions to amplify the wildtype AAC(6')-Iaa gene while introducing an average of 1.7 mutation per gene. Ten random clones were sequenced to determine the actual mutation frequency.

In each experiment, amplicons from the mutagenized pool were cloned into pACSE2 and the recombinant plasmids were electroporated into *E. coli* strain DH5α-E. The total number of transformants was estimated by plating serial dilutions of an aliquot of the transformation mixture onto L(tetracycline) medium, and the number of insert bearing clones was estimated by amplifying nine random transformants. The remainder of the culture was grown overnight in L-tetracycline medium to amplify the library of mutagenized AAC(6')-Iaa genes.

To screen the library for variants with increased resistance a number of cells equivalent to 10 times the library size was inoculated into bottles containing Muller-Hinton broth with two-fold increasing concentrations of drug. For each drug the lowest concentration was that that permitted growth of DH5α-E carrying wildtype plasmid pAA(6')-Iaa.

In seven independent experiments involving libraries of, respectively, $2.6 \times 10^6$, $2.9 \times 10^6$, $4.0 \times 10^6$, $1.7 \times 10^6$, $3.3 \times 10^6$, $1.0 \times 10^6$, and $3.3 \times 10^6$ mutagenized transformants, no mutants with increased resistance to any of the drugs tested were found.

Given the size of the coding region (437 bp), the average mutation frequency (1.7 mutations per gene), and the sizes of the above-listed libraries, those experiments are sufficient to give 100% confidence that all possible single mutants were screened, and 98% confidence that all possible double mutants were screened. In nature, variants typically arise as single mutants and extremely rarely as double mutants. Given that no single or double mutants increase resistance, confidence is very high that the AAC(6')-Iaa chromosomal gene of *Salmonella enteritidis* will not evolve to provide resistance to either gentamycin or amikacin, nor will it evolve to provide a higher level of resistance to tobramycin or kanamycin.

Example 3

Construction of MOD3-pTac Transposon

Plasmid pMOD3-Trc was constructed as follows. The pTac promoter was amplified from plasmid pSE380 (Invitrogen, San Diego, Calif.) using primers such that the 3' end of each primer corresponds, respectively to bp 63–84 and to the complement of bp 226–250 of pSE380 and the 5' ends, respectively, to bp 355–379 and the complement of bp 390–412 of

```
Primer BFH445 (SEQ ID No: 4):

tgttctcgca tattggctcg aattcatccg ctcacaattc      50
cacacattat

Primer BFH446 (SEO ID No: 5):

ggtcgactct agaggatccc cgggagccat cggaagctgt      46
ggtatg
```

The resulting amplicon was used as the primers in a site-directed mutagenesis reaction using a Stratagene Quick-Change™ kit according to manufacturer's instructions. The result is integration of the pTac promoter from pSE380 into pMOD-3 by replacement of bp 380–389 of pMOD-3 with bp 63–250 of pSE380. The method is described in detail in Geiser et al., "Integration of PCR fragments at any specific site within cloning vectors without the use of restriction enzymes and DNA ligase," *Biotechniques* 31:88–90 (2001), which is hereby incorporated by reference in its entirety. Integration of the pTac promoter in the correct orientation was confirmed by DNA sequencing.

The MOD3-pTac transposon is produced from plasmid pMOD3-Trc by PCR amplification using primers PCR Forward Primer and PCR Reverse Primer (both available from Epicentre) according to manufacturer's instructions.

Example 4

Construction of GeneHunter<Cam> Transposon

Plasmid pGeneHunter<Cam> will be constructed from plasmid pMOD3-Trc by amplifying the chloramphenicol resistance gene (chloramphenicol acetyl transferase gene) from base pairs 3591–461 of plasmid pACYC184 (GenBank Accession X06403, which is hereby incorporated by reference in its entirety). The resulting amplicon will be integrated into plasmid pMOD3-Trc using the method of Geiser et al., "Integration of PCR fragments at any specific site within cloning vectors without the use of restriction enzymes and DNA ligase," *Biotechniques* 31:88–90 (2001), which is hereby incorporated by reference in its entirety. PCR primers will be constructed so that their respective 3' and 5' ends correspond to the upstream and downstream sequences of plasmid pACYC184 and the sequences of pMOD3-Trc described above.

The GeneHunter<Cam> transposon will be produced from plasmid pGeneHunter<Cam> by PCR amplification using primers PCR Forward Primer and PCR Reverse Primer (Epicentre) according to manufacturer's instructions.

Example 5

Transformation of *Salmonella enteritidis* Serovar *typhimurium* Using GeneHunter<Cam> Transposon:Transposase Complex Using the GeneHunter<Cam> transposon formed in Example 4 above, a transposon:transposase complex will be formed according to the manufacturer's instructions for use of the EZ::TN Transposase (Epicentre). The resulting GeneHunter<Cam> transposon:transposase complex will then be used to transform *Salmonella enteritidis* serovar *typhimurium* to determine whether a previously unidentified antibiotic resistance gene can confer a resistance phenotype to transformants.

A 40 μl aliquot of electrocompetent *Salmonella enteritidis* serovar *typhimurium* cell culture, stored at −80° C., will be thawed on ice, mixed with 4 μl of ice cold GeneHunter<Cam> transposon:transposase complex, introduced into an ice cold electroporation cuvette and pulsed with 1600 volts for 45 milliseconds using a BioRad electroporation device according to manufacturer's instructions. Immediately following electroporation, 1 ml of SOC medium at 30° C. will be mixed with the cells. The mixture will be added to a culture tube containing an additional 1 ml of SOC medium at room temperature and the tube will be incubated on a rotating drum at 37° C. for 90 minutes to permit expression of the chloramphenicol resistance gene.

Example 6

Selecting *Salmonella enteritidis* Serovar *typhimurium* Transformants Expressing Putative Resistance Gene Following electroporation as described in Example 5 and after allowing sufficient time for expression of the chloramphenicol resistance gene (or other resistance gene carried on analogous GeneHunter transposons), an aliquot of the culture will be serially diluted and the dilutions will be spread onto L-plates containing chloramphenicol. The number of colonies that appear the following day will be used to estimate the total number of chloramphenicol resistant transformants in the culture. That number is defined as the library size.

The remainder of the culture will be diluted into 100 ml of L-broth containing chloramphenicol and allowed to grow overnight to amplify the library.

For each putative drug resistance gene sought, an aliquot of the amplified library containing a number of cells equivalent to ten times the library size will be inoculated into medium containing the drug at a concentration four times higher than the MIC of the host strain for that drug. The drug-containing culture will be incubated overnight. If the resulting culture is turbid the following day, it will be evidence of a putative resistance gene. Cells from the turbid culture will be streaked onto solid media containing the drug at 4 times the MIC concentration and several single colonies will be isolated.

Each colony will be tested to determine the MIC for the selected drug. Colonies with significantly different MICs will be assumed to have activated different resistance genes and will be saved.

To identify the expressed resistance gene, genomic DNA will be prepared from each strain and sheared to give fragments of an average size of about 10 kilobase pairs. The sheared DNA will be self-ligated and the ligation mixture will be electroporated into *E. coli* strain EC100D pir+ (Epicentre) and chloramphenicol resistant transformants will be selected. In a pir+ strain the self-ligated, circularized DNA containing the GeneHunter<Cam> transposon and flanking DNA will replicate as a plasmid. Several transformants will be tested for the new resistance phenotype. Those transformants for which the transposon-flanking DNA includes an intact new resistance gene will exhibit the new resistance phenotype. Plasmid will be prepared from one such transformant and the plasmid will be sequenced using a primer that reads outward in the direction of transcription of the pTac promoter transcription.

Although the invention has been described in detail for the purposes of illustration, it is understood that such detail is solely for that purpose, and variations can be made therein by those skilled in the art without departing from the spirit and scope of the invention which is defined by the following claims.

What is claimed:

1. A method of identifying putative antibiotic resistance genes comprising:

isolating a microbial DNA molecule or cDNA which encodes a putative antibiotic resistance protein or polypeptide that does not confer an antibiotic resistance phenotype to the microbe from which the DNA or cDNA was isolated;

transforming a host cell with the microbial DNA molecule or cDNA under conditions effective to express the putative antibiotic resistance protein or polypeptide; and growing transformed host cells on a growth medium including the antibiotic agent, wherein proliferation of host cells indicates antibiotic resistance conferred by expression of the putative antibiotic resistance protein or polypeptide.

2. The method according to claim 1 further comprising:

identifying, prior to said isolating, the microbial DNA molecule or cDNA from a pool of chromosomally encoded microbial DNA molecules or their corresponding cDNAs.

3. The method according to claim 2 wherein said identifying comprises:

comparing the amino acid sequence of a known antibiotic resistance protein or polypeptide against a database of microbial protein or polypeptide sequences under conditions effective to obtain the amino acid sequence of the putative antibiotic resistance protein or polypeptide, wherein the obtained amino acid sequence is matched in the database with a nucleotide sequence of the microbial DNA molecule or cDNA.

4. The method according to claim 3 wherein said comparing comprises:

assessing whether the amino acid sequence of the known antibiotic resistance protein or polypeptide is similar to the amino acid sequence of the putative antibiotic resistance protein or polypeptide.

5. The method according to claim 3, wherein said comparing comprises:

assessing whether the putative antibiotic resistance protein or polypeptide comprises one or more functional domains which are conserved between both the putative antibiotic resistance protein or polypeptide and the known antibiotic resistance protein or polypeptide.

6. The method according to claim 3, wherein the known antibiotic resistance protein or polypeptide is selected from the group consisting of β-lactamases, aminoglycoside kinases, aminoglycoside acetylases, aminoglycoside adenylases, fluoroquinolone resistance proteins, macrolide resistance proteins, tetracycline and tetracycline-derivative resistance proteins, chloramphenicol and chloramphenicol-derivative resistance proteins, glycopeptide resistance proteins, and sulfonamide/trimethoprim resistance proteins.

7. The method according to claim 2, wherein said identifying comprises:

comparing the nucleotide sequence coding for a known antibiotic resistance protein or polypeptide against a database of microbial nucleotide sequences under conditions effective to obtain a nucleotide sequence of the microbial DNA molecule or cDNA.

8. The method according to claim 7, wherein said comparing comprises:

assessing whether the nucleotide sequence of the microbial DNA molecule or cDNA is similar to the nucleotide sequence coding for the known antibiotic resistance protein or polypeptide.

9. The method according to claim 7, wherein the known antibiotic resistance protein or polypeptide is selected from the group consisting of β-lactamases, aminoglycoside kinases, aminoglycoside acetylases, aminoglycoside adenylases, fluoroquinolone resistance proteins, macrolide resistance proteins, tetracycline and tetracycline-derivative resistance proteins, chloramphenicol and chloramphenicol-derivative resistance proteins, glycopeptide resistance proteins, and sulfonamide/trimethoprim resistance proteins.

10. The method according to claim 1, wherein said transforming comprises:
   inserting the microbial DNA molecule or cDNA into an expression vector and
   incorporating the expression vector into the host cell.

11. The method according to claim 10, wherein the expression vector is a plasmid.

12. The method according to claim 10, wherein said incorporating comprises transduction, conjugation, mobilization, or electroporation.

13. The method according to claim 1, wherein said transforming and said growing indicates that the putative antibiotic resistance protein or polypeptide does not confer antibiotic resistance, said method further comprises:
   introducing multiple mutations into the microbial DNA molecule or cDNA to produce a mutant microbial DNA molecule or cDNA encoding a multiply mutated putative antibiotic resistance protein or polypeptide and
   determining whether the mutant microbial DNA molecule or cDNA confers resistance against the antibiotic agent.

14. The method according to claim 13 wherein the mutant microbial DNA molecule or cDNA confers resistance against the antibiotic agent, said method further comprising:
   determining whether the mutant microbial DNA molecule or cDNA is likely to evolve through two or more independent mutation events.

15. The method according to claim 1 carried out for a plurality of antibiotic agents.

16. The method according to claim 1 which confirms that the microbial DNA molecule or cDNA confers resistance against the antibiotic agent, said method further comprising:
   introducing multiple mutations into the microbial DNA molecule or cDNA to produce a mutant microbial DNA molecule or cDNA encoding a multiply mutated putative antibiotic resistance protein or polypeptide; and
   determining whether the mutant microbial DNA molecule or cDNA confers increased resistance against the antibiotic agent or resistance against a second antibiotic agent.

17. The method according to claim 16 wherein the mutant microbial DNA molecule or cDNA confers increased resistance against the antibiotic agent or resistance against a second antibiotic agent, said method further comprising:
   determining whether the mutant microbial DNA molecule or cDNA is likely to evolve through two or more independent mutation events.

18. A method of identifying putative antibiotic resistance genes comprising:
   determining whether a microbial DNA molecule confers resistance against an antibiotic agent when the microbial DNA molecule is expressed in its native cell following transformation of said cell with a transposon comprising, in a single DNA molecule, a pair of inverted repeats at opposite ends of the single DNA molecule and a promoter region oriented in a manner that affords transcription of coding regions located outside of the transposon sequence following its insertion into the genomic DNA of said cell, and but for transformation of said cell the microbial DNA molecule does not confer antibiotic resistance to the native cell, and
   isolating the microbial DNA molecule or cDNA which confers resistance against the antibiotic agent.

19. The method according to claim 18, wherein said determining further comprises:
   growing transformed cells on a selection media comprising the antibiotic agent, wherein proliferation of transformed cells indicates that the microbial DNA molecule is expressed and confers resistance against the antibiotic agent.

20. The method according to claim 18, wherein said isolating comprises:
   copying the microbial DNA molecule that confers resistance against the antibiotic agent and
   sequencing the isolated microbial DNA molecule.

21. The method according to claim 18, wherein the transposon further comprises:
   an origin of replication located between the pair of inverted repeats, the origin of replication being operable in the cell.

22. The method according to claim 18, wherein the transposon further comprises:
   an antibiotic selection marker located between the pair of inverted repeats.

23. The method according to claim 18, wherein the promoter region is a pTac promoter.

24. The method according to claim 18, wherein said transformation of said cell comprises:
   preparing a transposon:transposase complex and
   performing electroporation on the cell to cause uptake of the transposon:transposase complex.

25. The method according to claim 19, wherein the selection media used during said growing comprises a plurality of antibiotic agents.

26. The method according to claim 18 further comprising:
   introducing multiple mutations into the microbial DNA molecule or cDNA to produce a mutant microbial DNA molecule or cDNA encoding a multiply mutated antibiotic resistance protein or polypeptide and
   determining whether the mutant microbial DNA molecule or cDNA confers increased resistance against the antibiotic agent or resistance against a second antibiotic agent.

27. The method according to claim 26, wherein the mutant microbial DNA molecule or cDNA confers increased resistance against the antibiotic agent or resistance against a second antibiotic agent, said method further comprises:
   determining whether the mutant microbial DNA molecule or cDNA is likely to evolve through two or more independent mutation events.

28. A method of identifying putative antibiotic resistance genes comprising, in combination:
   (A) identifying a microbial DNA molecule or cDNA from a pool of chromosomal, microbial DNA molecules or their corresponding cDNAs, the microbial DNA molecule or cDNA encoding a putative antibiotic resistance protein or polypeptide, which microbial DNA or cDNA does not confer a resistance phenotype to the mocrobial source thereof,
   isolating the microbial DNA molecule or cDNA, and determining whether the microbial DNA molecule or cDNA confers to a first host cell resistance against an antibiotic agent; and (B) introducing a transposon into genomic DNA of a second host cell of the same species from which the microbial DNA molecule or cDNA was isolated in (A), the transposon comprising, in a single DNA molecule, a pair of inverted repeats at opposite ends of the DNA molecule and a promoter region which is oriented in a manner that affords transcription of coding regions located outside of the transposon sequence following its insertion into the genomic DNA, and growing transformed host cells on a selection media comprising an antibiotic agent, wherein proliferation of host cells indicates that the microbial DNA molecule is expressed and confers resistance against the antibiotic agent.

* * * * *

SEQUENCE LISTING

<160> NUMBER OF SEQ ID NOS: 5

<210> SEQ ID NO 1
<211> LENGTH: 438
<212> TYPE: DNA
<213> ORGANISM: Salmonella enteritidis

<400> SEQUENCE: 1

```
atggacatca ggcaaatgaa cagaacccat ctggatcact ggcgcggatt gcgaaaacag      60
ctctggcctg gtcacccgga tgacgcccat ctggcggacg gcgaagaaat tctgcaagcc     120
gatcatctgg catcatttat tgcgatggca gacggggtgg cgattggctt tgcggatgcc     180
tcaatccgcc acgattatgt caatggctgt gacagttcgc ccgtggtttt ccttgaaggt     240 attttttgttc tcccctcatt ccgtcaacgc ggcgtagcga aacaattgat tgcagcggtg     300
caacgatggg gaacgaataa agggtgtcgg gaaatggcct ccgataccct gccggaaaat     360
acaatttccc agaaagttca tcaggcgtta ggatttgagg aaacagagcg cgtcattttc     420
taccgaaagc gttgttga                                                  438
```

<210> SEQ ID NO 2
<211> LENGTH: 758
<212> TYPE: DNA
<213> ORGANISM: Artificial Sequence
<220> FEATURE:
<223> OTHER INFORMATION: Description of Artificial Sequence: MOD3-pTac transposon

<400> SEQUENCE: 2

```
attcaggctg cgcaactgtt gggaagggcg atcggtgcgg gcctcttcgc tattacgaca      60
gctgtctctt atacacatct caaccatcat cgatgaattt tctcgggtgt tctcgcatat     120
tggctcgaat tcatccgctc acaattccac acattatacg agccggatga ttaattgtca     180
acagctcatt tcagaatatt tgccagaacc gttatgatgt cggcgcaaaa aacattatcc     240
agaacgggag tgcgccttga gcgacacgaa ttatgcagtg atttacgacc tgcacagcca     300
```

```
taccacagct tccgatggct cccggggatc ctctagagtc gacctgcagg catgcaagct    360
ttaaaagcct tatatattct ttttttctt ataaaactta aaaccttaga ggctatttaa     420
gttgctgatt tatattaatt ttattgttca aacatgagag cttagtacgt gaaacatgag    480
agcttagtac gttagccatg agagcttagt acgttagcca tgagggttta gttcgttaaa    540
catgagagct tagtacgtta aacatgagag cttagtacgt gaaacatgag agcttagtac    600
gtactatcaa caggttgaac tgccaacgac tacgcactag ccaacaagag cttcagggtt    660
gagatgtgta taagagacag ctgtcttaat gaatcggcca acgcgcgggg agaggcggtt    720
tgcgtattgg gcgctcttcc gcttcctcgc tcactgac                            758

<210> SEQ ID NO 3
<211> LENGTH: 1864
<212> TYPE: DNA
<213> ORGANISM: Artificial Sequence
<220> FEATURE:
<223> OTHER INFORMATION: Description of Artificial Sequence:
      GeneHunter<Cam> transposon

<400> SEQUENCE: 3
attcaggctg cgcaactgtt gggaagggcg atcggtgcgg gcctcttcgc tattacgaca     60
gctgtctctt atacacatct caaccatcat cgatgaattt tctcgggtgt tctcgcatat    120
tggctcgaat tcatccgctc acaattccac acattatacg agccggatga ttaattgtca    180
acagctcatt tcagaatatt tgccagaacc gttatgatgt cggcgcaaaa aacattatcc    240
agaacgggag tgcgccttga gcgacacgaa ttatgcagtg atttacgacc tgcacagcca    300
taccacagct tccgatggct cccggggatc ctctagagtc gaccgtaagt tggcagcatc    360
acccgacgca ctttgcgccg aataaatacc tgtgacggaa gatcacttcg cagaataaat    420
aaatcctggt gtccctgttg ataccgggaa gccctgggcc aacttttggc gaaaatgaga    480
cgttgatcgg cacgtaagag gttccaactt caccataat gaaataagat cactaccggg     540
cgtatttttt gagttatcga gattttcagg agctaaggaa gctaaaatgg agaaaaaaat    600
cactggatat accaccgttg atatatccca atggcatcgt aaagaacatt ttgaggcatt    660
tcagtcagtt gctcaatgta cctataacca gaccgttcag ctggatatta cggccttttt    720
aaagaccgta aagaaaaata agcacaagtt ttatccggcc tttattcaca ttcttgcccg    780
cctgatgaat gctcatccgg aattccgtat ggcaatgaaa gacggtgagc tggtgatatg    840
ggatagtgtt cacccttgtt acaccgtttt ccatgagcaa actgaaacgt tttcatcgct    900
ctggagtgaa taccacgacg atttccggca gtttctacac atatattcgc aagatgtggc    960
gtgttacggt gaaaacctgg cctatttccc taaagggttt attgagaata tgttttttcgt   1020 ctcagccaat ccctgggtga gtttcaccag ttttgattta aacgtggcca atatggacaa    1080
cttcttcgcc cccgttttca ccatgggcaa atattatacg caaggcgaca aggtgctgat    1140
gccgctggcg attcaggttc atcatgccgt ctgtgatggc ttccatgtcg cagaatgct     1200 taatgaatta aacagtact gcgatgagtg cagggcggg gcgtaatttt tttaaggcag      1260
ttattggtgc ccttaaacgc ctggtgctac gcctgaataa gtgataataa gcggatgaat    1320
ggcagaaatt cgaaagcaaa ttcgacccgg tcgtcggttc agggcagggt cgttaaatag    1380
ccgcttatgt ctattgctgg tttaccggtt tattgactac cggaagcagt gtgaccgtgt    1440
gcttctcaaa tgcctgaggc caagctttaa aagccttata tattctttt tttcttataa     1500 aacttaaaac cttagaggct atttaagttg ctgatttata ttaattttat tgttcaaaca    1560
```

-continued

```
tgagagctta gtacgtgaaa catgagagct tagtacgtta gccatgagag cttagtacgt    1620
tagccatgag ggtttagttc gttaaacatg agagcttagt acgttaaaca tgagagctta    1680
gtacgtgaaa catgagagct tagtacgtac tatcaacagg ttgaactgcc aacgactacg    1740
cactagccaa caagagcttc agggttgaga tgtgtataag agacagctgt cttaatgaat    1800
cggccaacgc gcggggagag gcggtttgcg tattgggcgc tcttccgctt cctcgctcac    1860
tgac                                                                1864

<210> SEQ ID NO 4
<211> LENGTH: 50
<212> TYPE: DNA
<213> ORGANISM: Artificial Sequence
<220> FEATURE:
<223> OTHER INFORMATION: Description of Artificial Sequence: Primer

<400> SEQUENCE: 4
tgttctcgca tattggctcg aattcatccg ctcacaattc cacacattat              50

<210> SEQ ID NO 5
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 5
ggtcgactct agaggatccc cgggagccat cggaagctgt ggtatg                  46
```